United States Patent
Boyajian et al.

(10) Patent No.: US 11,446,512 B2
(45) Date of Patent: Sep. 20, 2022

(54) ADJUSTABLE ILLUMINATOR FOR PHOTODYNAMIC THERAPY AND DIAGNOSIS

(71) Applicant: DUSA Pharmaceuticals, Inc., Wilmington, MA (US)

(72) Inventors: Thomas Boyajian, Wilmington, MA (US); Mark Carota, Chelmsford, MA (US); Brian Mazejka, Salem, NH (US)

(73) Assignee: DUSA PHARMACEUTICALS, INC., Billerica, MA (US)

( * ) Notice: Subject to any disclaimer, the term of this patent is extended or adjusted under 35 U.S.C. 154(b) by 5 days.

(21) Appl. No.: 16/791,004

(22) Filed: Feb. 14, 2020

(65) Prior Publication Data
US 2020/0246630 A1  Aug. 6, 2020

Related U.S. Application Data

(62) Division of application No. 15/292,731, filed on Oct. 13, 2016, now Pat. No. 10,589,122.
(Continued)

(51) Int. Cl.
*A61N 5/06* (2006.01)
*A61B 5/00* (2006.01)

(52) U.S. Cl.
CPC ............ *A61N 5/062* (2013.01); *A61B 5/0064* (2013.01); *A61B 5/0082* (2013.01);
(Continued)

(58) Field of Classification Search
CPC ........ A61N 5/06; A61N 5/062; A61N 5/0616; A61N 2005/0626; A61N 2005/0652;
(Continued)

(56) References Cited

U.S. PATENT DOCUMENTS

| 5,032,400 A | 7/1991 | Wiersum et al. |
| 5,211,938 A | 5/1993 | Kennedy et al. |

(Continued)

FOREIGN PATENT DOCUMENTS

| DE | 69827286 T2 | 11/2005 |
| EP | 1 238 652 A1 | 9/2002 |

(Continued)

OTHER PUBLICATIONS

Braathen, Lasse R., et al. "Guidelines on the Use of Photodynamic Therapy for Nonmelanoma Skin Cancer: an International Consensus." Journal of the American Academy of Dermatology 56.1, Jan. 2007, pp. 125-143.

(Continued)

*Primary Examiner* — Tammie K Marlen
(74) *Attorney, Agent, or Firm* — Foley & Lardner LLP

(57) ABSTRACT

An adjustable illuminator for photodynamically diagnosing or treating a surface includes a plurality of first panels and at least one second panel. The plurality of first panels have wider widths and the at least one second panel has a narrower width. The narrower width is less than the wider widths. The illuminator further includes a plurality of light sources, each mounted to one of the plurality of first panels or the at least one second panel and configured to irradiate the surface with substantially uniform intensity visible light. The plurality of first panels and the at least one second panel are rotatably connected. The at least one second panel is connected on each side to one of the plurality of first panels. The second panel acts as a "lighted hinge" to reduce or eliminate optical dead spaces between adjacent panels when the illuminator is bent into a certain configuration.

20 Claims, 8 Drawing Sheets

Related U.S. Application Data

(60) Provisional application No. 62/241,902, filed on Oct. 15, 2015.

(52) U.S. Cl.
CPC ............... *A61N 2005/0626* (2013.01); *A61N 2005/0633* (2013.01); *A61N 2005/0642* (2013.01); *A61N 2005/0651* (2013.01); *A61N 2005/0652* (2013.01); *A61N 2005/0662* (2013.01); *A61N 2005/0663* (2013.01)

(58) Field of Classification Search
CPC .... A61N 2005/0633; A61N 2005/0642; A61N 2005/0663; A61N 2005/0636; A61N 2005/064; A61N 2005/0658; A61N 2005/0651; A61N 2005/0662; A61B 5/0064; A61B 5/0082
See application file for complete search history.

(56) References Cited

U.S. PATENT DOCUMENTS

| | | | |
|---|---|---|---|
| 5,601,838 A | 2/1997 | Hind | |
| 5,686,065 A | 11/1997 | Haney | |
| 5,814,008 A | 9/1998 | Chen et al. | |
| 5,849,027 A | 12/1998 | Gart et al. | |
| 6,223,071 B1 | 4/2001 | Lundahl et al. | |
| 6,559,183 B1 | 5/2003 | Schmid et al. | |
| 6,709,446 B2 | 3/2004 | Lundahl et al. | |
| 6,897,238 B2 | 5/2005 | Anderson | |
| 7,033,381 B1 | 4/2006 | Larsen | |
| 7,156,865 B2 | 1/2007 | Waldmann | |
| 7,190,109 B2 | 3/2007 | Lundahl et al. | |
| 7,723,910 B2 | 5/2010 | Lundahl et al. | |
| 7,730,893 B2 | 6/2010 | Dougal | |
| 8,030,836 B2 | 10/2011 | Lundahl et al. | |
| 8,216,289 B2 | 7/2012 | Lundahl et al. | |
| 8,226,289 B2 | 7/2012 | Lindeberg | |
| 8,758,418 B2 | 6/2014 | Lundahl et al. | |
| 9,108,045 B2 | 8/2015 | Sakamoto et al. | |
| 9,227,082 B2 | 1/2016 | McDaniel | |
| 9,533,170 B2 | 1/2017 | Dye et al. | |
| 10,357,567 B1 | 7/2019 | Lundahl et al. | |
| 11,135,293 B2 | 10/2021 | Lundahl et al. | |
| 2001/0021812 A1 | 9/2001 | Lundahl et al. | |
| 2003/0088296 A1 | 5/2003 | Waldmann | |
| 2003/0216795 A1* | 11/2003 | Harth ............... | A61N 5/062 607/88 |
| 2004/0010299 A1 | 1/2004 | Tolkoff et al. | |
| 2004/0162596 A1 | 8/2004 | Altshuler et al. | |
| 2004/0260365 A1 | 12/2004 | Groseth et al. | |
| 2005/0075703 A1 | 4/2005 | Larsen | |
| 2005/0090877 A1 | 4/2005 | Harth et al. | |
| 2006/0241726 A1 | 10/2006 | Whitehurst | |
| 2006/0253175 A1 | 11/2006 | Fan et al. | |
| 2006/0287696 A1 | 12/2006 | Wright et al. | |
| 2007/0283655 A1 | 12/2007 | Tobin | |
| 2008/0031924 A1 | 2/2008 | Gilson et al. | |
| 2008/0188558 A1 | 8/2008 | Godal et al. | |
| 2009/0247932 A1 | 10/2009 | Barolet | |
| 2009/0324727 A1 | 12/2009 | Foguet Roca | |
| 2010/0010591 A1 | 1/2010 | Daffer | |
| 2010/0174222 A1 | 7/2010 | McDaniel | |
| 2010/0174223 A1 | 7/2010 | Sakamoto et al. | |
| 2010/0298758 A1 | 11/2010 | Christiansen et al. | |
| 2011/0020441 A1 | 1/2011 | Klaveness et al. | |
| 2011/0053965 A1 | 3/2011 | Trigiante | |
| 2011/0106222 A1 | 5/2011 | Wilson et al. | |
| 2011/0224598 A1 | 9/2011 | Barolet | |
| 2011/0293528 A1 | 12/2011 | Godal et al. | |
| 2012/0283328 A1 | 11/2012 | Modi | |
| 2012/0287671 A1 | 11/2012 | Parker et al. | |
| 2013/0066404 A1* | 3/2013 | Tapper ............... | A61N 5/0616 607/90 |
| 2013/0066405 A1 | 3/2013 | Dougal | |
| 2013/0190845 A1 | 7/2013 | Liu et al. | |
| 2013/0274834 A1 | 10/2013 | Barolet et al. | |
| 2013/0289089 A1 | 10/2013 | Morris et al. | |
| 2013/0304019 A1 | 11/2013 | Cooper et al. | |
| 2013/0315999 A1 | 11/2013 | Paithankar et al. | |
| 2014/0010761 A1 | 1/2014 | Parent et al. | |
| 2014/0067024 A1 | 3/2014 | Jones et al. | |
| 2015/0162109 A1 | 6/2015 | Nager | |
| 2015/0238776 A1 | 8/2015 | Sakamoto et al. | |
| 2015/0290028 A1 | 10/2015 | Isserow et al. | |
| 2015/0290470 A1 | 10/2015 | Tapper et al. | |
| 2016/0008623 A1 | 1/2016 | Jones et al. | |
| 2016/0030565 A1 | 2/2016 | Wulf et al. | |
| 2016/0045757 A1 | 2/2016 | Groseth | |
| 2016/0166846 A1 | 6/2016 | Chae | |
| 2016/0175609 A1 | 6/2016 | Dye et al. | |
| 2016/0175610 A1 | 6/2016 | Livingston et al. | |
| 2016/0346392 A1 | 12/2016 | Wulf | |
| 2019/0290763 A1 | 9/2019 | Lundahl et al. | |
| 2020/0100997 A1 | 4/2020 | Soler et al. | |
| 2020/0261580 A1 | 8/2020 | Willey | |
| 2020/0269063 A1 | 8/2020 | Boyajian et al. | |
| 2020/0398071 A1 | 12/2020 | Boyajian et al. | |

FOREIGN PATENT DOCUMENTS

| | | |
|---|---|---|
| JP | H04-500770 A | 2/1992 |
| JP | 2002-529495 A | 9/2002 |
| JP | 2010-515714 A | 5/2010 |
| WO | WO-93/09847 A1 | 5/1993 |
| WO | WO-96/06602 A1 | 3/1996 |
| WO | WO-99/22802 A1 | 5/1999 |
| WO | WO-02/13788 A1 | 2/2002 |
| WO | WO-2007/112427 A2 | 10/2007 |
| WO | WO-2009/003173 A1 | 12/2008 |
| WO | WO-2011/124912 A1 | 10/2011 |
| WO | WO-2013/110021 A1 | 7/2013 |
| WO | WO-2014/131115 A1 | 9/2014 |
| WO | WO-2015/041919 A1 | 3/2015 |
| WO | WO-2019/018408 A1 | 1/2019 |

OTHER PUBLICATIONS

Dragieva, G. et al., "A Randomized Controlled Clinical Trial of Topical Photodynamic Therapy with Methyl Aminolaevulinate in the Treatment of Actinic Keratoses in Transplant Recipients." British Journal of Dermatology 151.1, Jul. 2004, pp. 196-200.

Kurwa, Habib A., et al., "A Randomized Paired Comparison of Photodynamic Therapy and Topical 5-Fluorouracil in the Treatment of Actinic Keratoses." Journal of the American Academy of Dermatology 41.3, Sep. 1999, pp. 414-418.

Maccormack, Mollie A., "Photodynamic Therapy in Dermatology: An Update on Applications and Outcomes." Seminars in Cutaneous Medicine and Surgery. vol. 27, No. 1, WB Saunders, Mar. 2008, pp. 52-62.

Ozog, David M., et al., "Photodynamic Therapy: A Clinical Consensus Guide." Dermatologic Surgery 42.7, Jul. 2016, pp. 804-827.

Wolf, Peter, et al., "Topical Photodynamic Therapy With Endogenous Porphyrins After Application of 5-Aminolevulinic Acid: An Alternative Treatment Modality for Solar Keratoses, Superficial Squamous Cell Carcinomas, and Basal Cell Carcinomas?" Journal of the American Academy of Dermatology 28.1, Jan. 1993, pp. 17-21.

Extended European Search Report, Application No. 20214586.8, dated Jun. 2, 2021, 8 pages.

USPTO Notice of Allowance, U.S. Appl. No. 16/438,702, dated May 20, 2021, 10 pages.

Daniel Barolet et al., Radiant Near Infrared Light Emitting Diode Exposure as Skin Preparation to Enhance Photodynamic Therapy Inflammatory Type Acne Treatment Outcome, Lasers in Surgery and Medicine vol. 42, No. 2, Feb. 1, 2010, pp. 171-178.

Extended European Search Report, Application No. 18835929.3, dated Mar. 12, 2021, 10 pages.

(56) References Cited

OTHER PUBLICATIONS

Johanna T.H.M. Van Den Akker et al., Effect of Elevating the Skin Temperature During Topical ALA Application on in vitro ALA penetration Through Mouse Skin and in vivo PpIX production in Human Skin, Photochemical and Photobiological Sciences, Royal Society of Chemistry, Cambridge, GB, vol. 3, No. 3, Mar. 1, 2004, pp. 263-267.
Petras Juzenas et al., Uptake of Topically Applied 5-Aminolevulinic Acid and Production of Protoporphyrin IX in Normal Mouse Skin: Dependence on Skin Temperature, Photochemistry and photobiology, vol. 69, No. 4, Apr. 1, 1999, pp. 478-481.
International Search Report from PCT/US2018/042505, dated Oct. 2, 2018.
USPTO Notice of Allowance, U.S. Appl. No. 16/438,702, dated Mar. 22, 2021, 14 pages.
USPTO Office Action, U.S. Appl. No. 17/009,871, dated Mar. 23, 2021, 9 pages.
USPTO Office Action, U.S. Appl. No. 17/109,311, dated Mar. 2, 2021, 16 pages.
USPTO Notice of Allowance, U.S. Appl. No. 17/009,871, dated Jul. 22, 2021, 14 pages.
USPTO Notice of Allowance, U.S. Appl. No. 17/109,311, dated Aug. 10, 2021, 14 pages.
USPTO Office Action, U.S. Appl. No. 17/109,311, dated Jul. 20, 2021, 17 pages.
U.S. Appl. No. 17/109,311, filed Dec. 2, 2020, Lundahl et al.
USPTO Office Action, U.S. Appl. No. 17/009,871, dated Dec. 2, 2020, 15 pages.
Britannica, The Editors of Encyclopaedia, "Gel: Physics and Chemistry", 4 pages, Jul. 20, 1998, and "Gel: Additional Information", 1 page, Available on line at: https://www.britannica.com/science/gel and https://www.britannica.com/science/gel/additional-info#history.
Fehr et al., Photodynamic Therapy of Vulvar and Vaginal Condyloma and Intraepithelial Neoplasia Using Topically Applied 5-Aminolevulinic Acid, Lasers in Surgery and Medicine, 2002, 30:273-279, 7 pages.
Fehr et al., Selective Photosensitizer Distribution in Vulvar Condyloma Acuminatum After Topical Application of 5-Aminolevulinic Acid, Am. J. Obstet. Gynecol., vol. 174(3), Mar. 1996, pp. 951-957.
Hurlimann et al., Photodynamic Therapy of Superficial Basal Cell Carcinomas Using Topical 5-Aminolevulinic Acid in a Nanocolloid Lotion, Pharmacology and Treatment, Dermatology 197, 1998, pp. 248-254.
Reinhold et al., A Randomized, Double-Blind, Phase III, Multicentre Study to Evaluate the Safety and Efficacy of BF-200 ALA (Ameluz®) vs. Placebo in the Field-Directed Treatment of Mild-to-Moderate Actinic Keratosis with Photodynamic Therapy (PDT) When Using the BF-RhodoLED® Lamp, British Journal of Dermatology, 175(4): 696-705, Feb. 27, 2016, 10 pages.
Third Party Submission filed in U.S. Appl. No. 17/109,311, filed Jun. 21, 2021, 21 pages.
USPTO Office Action, U.S. Appl. No. 16/438,702, dated Oct. 13, 2020, 17 pages.
Letter to UVBiotek, LLC, dated Jul. 28, 2017, Re: K170187, Trade/Device Name: Photodynamic Therapy Device, available at https://www.accessdata.fda.gov/cdrh_docs/pdf17/K170187.pdf (accessed Apr. 30, 2020).
Webpage printout, Hill Laboratories Company, "Aklarus Phototherapy Treatment System with Red, Blue and Infrared Wavelengths by Hill Therapeutics," available at https://hilllabs.com/therapeutics/Aklarus-Photo-Therapy-System.php (accessed Apr. 30, 2020).
Australian Office Action, Application No. 2019200152, dated Nov. 11, 2019, 9 pages.
European Office Action, Application No. 16787667.1, dated Sep. 24, 2019, 5 pages.
GLAD.com.au: "GLAD History", 2012, [online] URL: http://www.glad.com.au/about-glad/glad-history/, retrieved online Nov. 8, 2019.
International Preliminary Reporton Patentability, PCT/US2016/056572, dated Apr. 26, 2018, 9 pages.
International Preliminary Reporton Patentability, PCT/US2018/027070, dated Oct. 24, 2019, 10 pages.
Notice of Allowance, U.S. Appl. No. 15/487,991, dated Jan. 15, 2020, 11 pages.
Notice of Allowance, U.S. Appl. No. 15/487,991, dated Oct. 2, 2019, 16 pages.
International Search Report and Written Opinion International Application No. PCT/US2018/027070, dated Oct. 16, 2018, 18 pages.
Partial International Search, Annex to Form PCT/ISA/206, International Application No. PCT/US2018/027070, dated Jul. 19, 2018, 10 pages.
USPTO Advisory Action, U.S. Appl. No. 15/487,991, dated May 15, 2018, 5 pages.
USPTO Interview Summary, U.S. Appl. No. 15/487,991, dated Sep. 22, 2017, 4 pages.
USPTO Notice of Allowance, U.S. Appl. No. 15/292,731, dated Nov. 14, 2019, 12 pages.
USPTO Office Action, U.S. Appl. No. 15/487,991, dated Jul. 31, 2018, 20 pages.
USPTO Office Action, U.S. Appl. No. 15/487,991, dated Apr. 9, 2019, 27 pages.
USPTO Office Action, U.S. Appl. No. 15/487,991, dated Jun. 12, 2017, 22 pages.
USPTO Office Action, U.S. Appl. No. 15/487,991, dated Feb. 6, 2018, 19 pages.
Affidavit of Duncan Hall, Aug. 10, 2021.
Agostinis et al. Photodynamic therapy of cancer: an update. CA: A Cancer Journal for Clinicians. May 2011; 61(4):250-2.
Aktilite CL128 Operators Manual with Metvixia, Revised 2008.
Ameluz, Prescribing Information (2016).
Berardesca E, Vignoli GP, Fideli D, Maibach H. Effect of occlusive dressings on the stratum corneum water holding capacity. The American Journal of the Medical Sciences. Jul. 1992;304(1):25-28.
Bissonnette R. Photodynamic therapy. In: Gold M.H., editor. Photodynamic Therapy in Dermatology. Springer Science and Business Media, LLC; New York, NY, USA: 2011. pp. 221-229.
Blu-U, Operating Manual (2006).
Calderhead RG. Light-emitting diode phototherapy in dermatological practice in lasers in dermatology and medicine. Lasers in Dermatology and Medicine. Aug. 2011:231-265.
CV of Dr. Howard Rogers MD, PHD.
Declaration of Dr. Howard Rogers MD, PHD, Oct. 19, 2021.
DUSA Levulan Press Release, Dec. 6, 1999.
European Medicines Agency CHMP Assessment Report (excerpts), Oct. 20, 2011.
Fauteck Europe PMC Website Database Listing, Oct. 25, 2007.
Fauteck JD, Ackermann G, Birkel M, Breuer M, Moor AC, Ebeling A, Ortland C. Fluorescence characteristics and pharmacokinetic properties of a novel self-adhesive 5-ALA patch for photodynamic therapy of actinic keratoses, 2008.
Harris DR. Percutaneous absorption and the surface area of occluded skin: a scanning electron microscopic study. British Journal of Dermatology. 1974; 91(27-32).
Hongcharu W., Taylor C., Chang, Y., Aghasi, D., Suthamjariya, K., Anderson, R. Topical ALA-photodynamic therapy for the treatment of acne vulgaris. J Invest Dermatol. Aug. 2000;115(2):183-92.
International Patent Reviews, LLC review of U.S. Pat. No. 10,357,567 dated Jul. 26, 2021.
Jeffes E., McCullough J., Weinstein G., Fergin P., Nelson J., Shull T., Simpson K., Bukaty L., Hoffman W., Fong N. Photodynamic therapy of actinic keratosis with topical 5-aminolevulinic acid. A pilot dose-ranging study. Arch Dermatol. 1997.
Levulan, Label (2002).
Levulan, Label (2009).
MacCormack MA. Photodynamic therapy in dermatology: an update on applications and outcomes. Semin Cutan Med Surg. Mar. 2008;27(1):52-62.
McLaren G. Photodynamic therapy. In; Pfenninger and Fowler's procedures for primary care. Third Ed. Mosby Elsevier; Philadelphia, PA: 2011. pp 397-400.
News article entitled DUSA Pharmaceuticals To Pay U.S. $20.75 Million To Settle False Claims Act Allegations Relating To Promotion Of Unsupported Drug Administration Process, Aug. 24, 2020.

(56) References Cited

OTHER PUBLICATIONS

Ozog, D., Rkein, A., Fabi, S., Gold M., Goldman, M., Lowe, N., Martin, G., Munavalli, G. Photodynamic therapy: A clinical consensus guide. Dermatol Surg. Jul. 2016;42(7):804-27.
Palm M., Goldman PM. Aminolevulinic acid: actinic keratosis and photorejuvenation. In: Gold M.H., editor. Photodynamic Therapy in Dermatology. Springer Science and Business Media, LLC. Nov. 2011:5-30.
Petition for Inter Partes Review Under 35 U.S.C. 312, Oct. 19, 2021.
Rick K, Sroka R, Stepp H, Kriegmair M, Huber RM, Jacob K, Baumgartner R. Pharmacokinetics of 5-aminolevulinic acidinduced protoporphyrin IX in skin and blood. J Photochem Photobiol B. Oct. 1997;40(3):313-9.
Sakamoto FH, Torezan L, Anderson RR. Photodynamic therapy for acne vulgaris: a critical review from basics to clinical practice: part II. Understanding parameters for acne treatment with photodynamic therapy. J Am Acad Dermatol. Aug. 2010;63(2):195-211.
Sotiriou E, Apalla Z, Maliamani F, Zaparas N, Panagiotidou D, Ioannides D. Intraindividual, right-left comparison of topical 5-aminolevulinic acid photodynamic therapy vs. 5% imiquimod cream for actinic keratoses on the upper extremities, 2009.
Sotiriou Pubmed Website Database Listing, Sep. 23, 2009.
Wachowska et al., Aminolevulinic acid (ALA) as a prodrug in photodynamic therapy of cancer. Molecules. May 2011; 16(5): 4140-4164.
Willey A, Anderson RR, Sakamoto FH. Temperature-modulated photodynamic therapy for the treatment of actinic keratosis on the extremities. Dermatologic Surgery. Oct. 2014;40(10):1094-1102.
Willey Pubmed Website Database Listing, Oct. 2014.
Wolf P., Rieger E. and Kerl H. Topical photodynamic therapy with endogenous porphyrins after application of 5-aminolevulinic acid: an alternative treatment modality for solar keratoses, superficial squamous cell carcinomas, and basal cell carcinomas?, Jan. 1993.
Japanese Office Action and English translation, Application No. 2019-555822, dated Jan. 11, 2022, 13 pages.
USPTO Office Action, U.S. Appl. No. 16/808,631, dated Jan. 21, 2022, 28 pages.
Australian Examination Report, Application No. 2020267186, dated Nov. 19, 2021, 6 pages.
USPTO Office Action, U.S. Appl. No. 17/487,698, dated Dec. 17, 2021, 21 pages.
Zhang et al., "Topical 5-Aminolevulinic Photodynamic Therapy with Red Light vs Intense Pulsed Light for the Treatment of Acne Vulgaris _ A Spilit Face, Randomized, Prospective Study," Dermato-Endocrinology, 2018, vol. 9, No. 1, e1375634 (9 pages).
Australian Examination Report, Application No. 2020267186, dated Feb. 3, 2022, 4 pages.
Australian Examination Report, Application No. 2021107564, dated Apr. 4, 2022, 4 pages.
Notice of Allowance, U.S. Appl. No. 17/487,698, dated Apr. 29, 2022, 11 pages.
Maisch et al., Fluorescence Induction of Protoporphyrin IX by a New 5-Aminolevulinic Acid Nanoemulsion Used for Photodynamic Therapy in a Full-Thickness ex vivo Skin Model, Experimental Dermatology, 19, 2009, pp. e302-e305.
Nucci et al., Treatment of Anogenital Condylomata Acuminata with Topical Photodynamic Therapy: Report of 14 Cases and Review, International Journal of Infectious Diseases, 14S, 2010, pp. e280-e282.
USPTO Non-Final Office Action, U.S. Appl. No. 16/631,205, dated Mar. 3, 2022, 31 pages.
Willey et al., American Society for Laser Medicine and Surgery Abstracts, #147, Ultra Fast Thermal PDT for Facial AKs: Proof of Concept Study, Mar. 2017, 2 pages.
U.S. Appl. No. 17/487,698, filed Sep. 28, 2021, Lundahl et al.
U.S. Appl. No. 17/506,849, filed Oct. 21, 2021, Boyajian et al.
Japanese Office Action and English Translation, Application No. JP 2020-503004, dated Aug. 2, 2022 (6 pages).

* cited by examiner

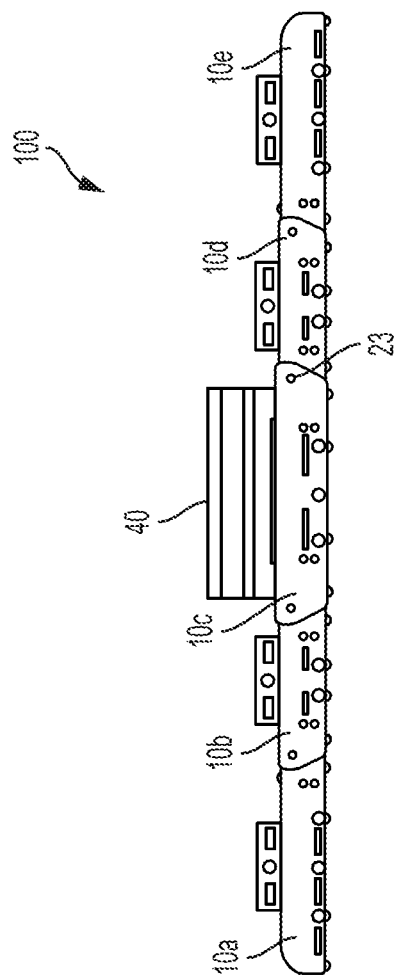
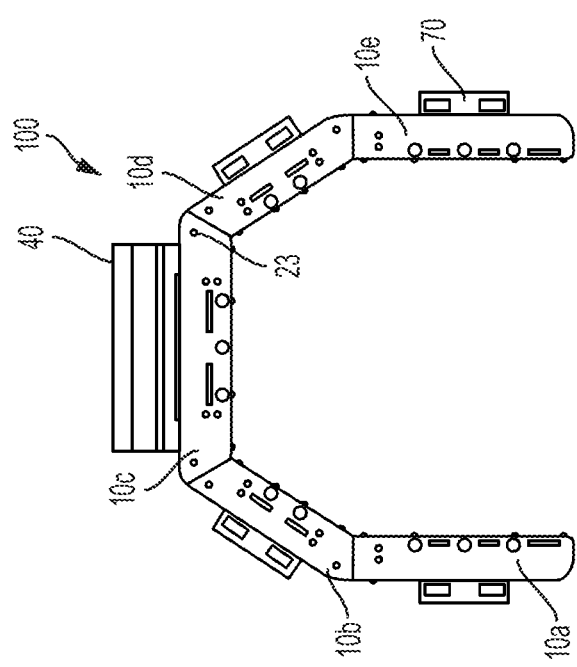

ADJUSTABLE ILLUMINATOR FOR PHOTODYNAMIC THERAPY AND DIAGNOSIS

CROSS-REFERENCE TO RELATED APPLICATIONS

This application is a divisional application of U.S. application Ser. No. 15/292,731, filed Oct. 13, 2016, now granted as U.S. Pat. No. 10,589,122, which claims the benefit of priority to U.S. Provisional Application No. 62/241,902 filed on Oct. 15, 2015, now expired, the entire contents of all of which are incorporated herein by reference.

FIELD

The invention relates generally to an adjustable illuminator that provides a uniform distribution of visible light in a number of configurations and is suitable for use in photodynamic therapy and diagnosis.

BACKGROUND

Photodynamic therapy (PDT), photodynamic diagnosis (PD), or photochemotherapy is generally used to treat and/or diagnose several types of ailments in or near the skin or other tissues, such as those in a body cavity. For example, PDT or PD may be used for treatment or diagnosis of actinic keratosis of the scalp or facial areas of a patient. In addition, PDT and PD may be used for treatment and diagnosis of other indications (e.g., acne, warts, psoriasis, photo-damaged skin, cancer) and other areas of the patient (e.g., arms, legs).

During one form of PDT or PD, a patient is first administered a photoactivatable agent or a precursor of a photoactivatable agent that accumulates in the tissue to be treated or diagnosed. The area in which the photoactivatable agent is administered is then exposed to visible light, which causes chemical and/or biological changes in the agent. These changes allow the agent to then selectively locate, destroy, or alter the target tissue while, at the same time, causing only mild and reversible damage to other tissues in the treatment area. One example of a precursor of a photoactivatable agent is 5-aminolevulinic acid ("ALA"), which is commonly used in PDT of actinic keratosis. As they are used here, the terms ALA or 5-aminolevulinic acid refer to ALA itself, precursors thereof and pharmaceutically acceptable salts of the same.

For effective treatment, it is desirable to have a power output that is uniform in intensity and color. Illuminators, such as those disclosed in U.S. Pat. Nos. 8,758,418; 8,216,289; 8,030,836; 7,723,910; 7,190,109; 6,709,446; 6,223,071, which are incorporated by reference in their entireties for the techniques, methods, compositions, and devices related to PDT and PD, are typically used to provide the proper uniformity of light for treatment purposes. These devices generally include a light source (e.g., a fluorescent tube), coupling elements that direct, filter or otherwise conduct emitted light so that it arrives at its intended target in a usable form, and a control system that starts and stops the production of light when necessary.

SUMMARY

Because PDT can be used to treat a variety of treatment areas, some illuminators utilize two or more panels, each panel having a light source to emit light at the intended target area. These panels are coupled together so as to be rotatable relative to each other. By incorporating multiple, rotatable panels, the overall size and shape of the area that is illuminated can be changed according to the intended treatment area.

In conventional adjustable illuminators, the panels are equally sized by width and length and are typically driven at the same power level. The panels are further joined at their edges by hinges so as to be rotatable to achieve a desired configuration. However, due to the edges of the panels and the presence of the hinges, the light source(s) of one panel does not immediately adjoin the light source(s) of an adjacent panel. As a result, light is not emitted from a "gap" between the light sources. The lack of light emitting from such areas, together with the uniform supply of power to the panels, can cause optical "dead space" in certain portions of the target treatment area. These portions, in turn, receive less overall light, resulting in a lower dose of treatment in those portions. In some instances, the dose of treatment can be lowered by as much as a factor of five when compared with those areas receiving an optimal amount of light.

Generally, these conventional illuminators are used for phototherapy of acne, which typically does not require the administration of a photoactivatable agent for effective treatment. Thus, exposure to the light alone is generally sufficient treatment. Moreover, because multiple treatment sessions can be utilized to effectively treat the condition, uniformity of light across the target area during a given treatment is less of a concern in some situations. However, some forms of treatment involving PDT, such as the use of ALA to treat actinic keratosis, require specific and highly uniform intensity and color of light to achieve effectiveness. In these instances, successful PDT relies on the targeted delivery of both the correct quantity of the photoactivatable agent and the correct quantity (i.e., power and wavelength) of light to produce the desired photochemical reactions in the target cells. Thus, to achieve this, the light source must provide illumination to the target area and this illumination must be uniform with respect to both wavelength and power. The optical dead space that can occur at or near the hinges of conventional adjustable illuminators reduces the uniformity of the light along the treatment area, thereby reducing the effectiveness of PDT for these specific treatments. Moreover, these illuminators are also configured to adjust within a limited range, such that only a limited amount of surfaces on a patient's body may be treated, such as a patient's face and scalp. In addition, due to the various contours of a patient's body, the uniformity of light delivered by these conventional illuminators may vary substantially depending on the treatment area of the patient.

Therefore, it is an object of some embodiments of the present invention to reduce or eliminate these dead spaces and provide for a more uniform light distribution in an adjustable illuminator designed for PDT or PD of a variety of targeted areas. In addition, it is an object of some embodiments of the present invention to provide an infinitely adjustable illuminator that can effectively deliver a uniformity of light across various areas of a patient's body, such as a patient's extremities (e.g., arms and legs) or torso, in addition to a patient's face and scalp. Thus, a uniform light may be delivered to a targeted treatment area regardless of the shape and location of the contoured surface of the patient's body.

One embodiment of the present invention uses a plurality of panels, wherein at least one panel is of a different width than the other panels. This panel is positioned between two other panels and, in a way, acts as a "lighted hinge" to provide enough "fill-in" light to reduce or eliminate the optical dead spaces when the panels are bent into a certain configuration. Preferably, five panels in total are used to provide for an optimal increase in the total size of possible treatment areas. Two of the panels are preferably of a smaller width than the other three larger panels. These panels are positioned in an alternating manner such that each of the smaller-width panels is situated in between two of the three larger panels to allow for both adjustability and increased uniformity. Furthermore, to further reduce or eliminate optical dead spaces, the panels are preferably coupled together using nested hinges, thereby reducing the area in which no light source is present on the illuminator. In order to even further reduce or eliminate optical dead spaces, it is preferable that the light sources on each of the panels are individually configurable to provide specific power output to certain areas of the light sources on the panels to compensate for decreased uniformity. For example, the power outputted to each individual diode in an array of light emitting diodes (LED) may be individually adjusted.

BRIEF DESCRIPTION OF THE DRAWINGS

Features, aspects, and advantages of the present invention will become apparent from the following description and the accompanying exemplary embodiments shown in the drawings, which are briefly described below.

FIGS. 1A-1B show top views of a main body of an illuminator according to an exemplary embodiment.

DETAILED DESCRIPTION

Figure 2B:
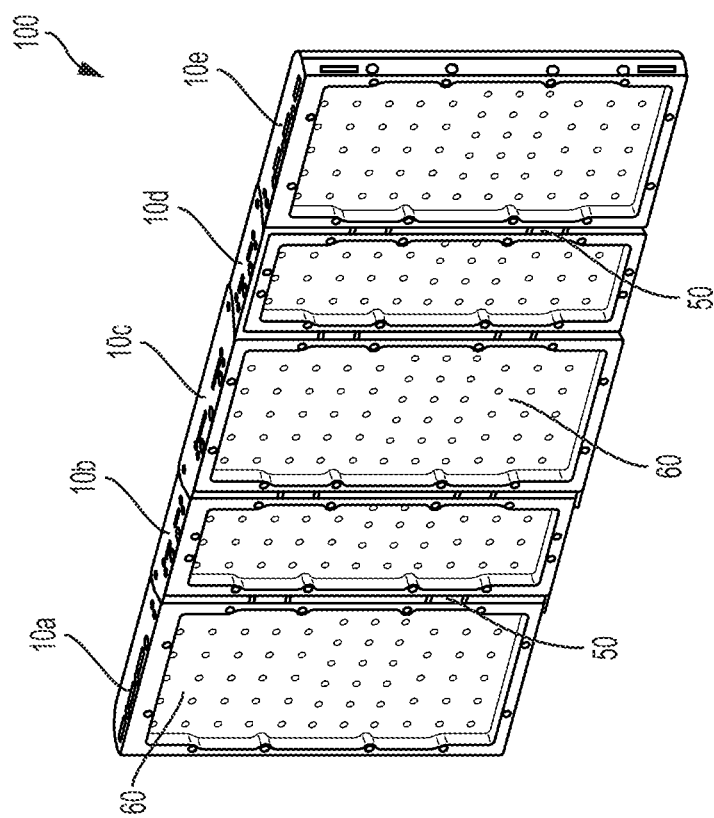
FIGS. 2A-2B show perspective views of the main body of the illuminator of FIGS. 1A-1B.

FIGS. 1A-1B and 2A-2B illustrate one embodiment of a configurable illuminator according to the present invention. The illuminator includes a main body 100, which preferably has five individual panels 10a-10e, each of which are connected in a rotatable manner via nested hinges 50. Each panel contains an array of light emitting diodes (LED) 60, which may be configured in an evenly spaced pattern across the face of the panel. The number of individual LEDs arranged in a given array is not particularly limited. Alternatively, other types of light sources may be used, such as fluorescent or halogen lamps.

Preferably, each LED array 60 extends as far to the edges as possible. In addition, the LED arrays 60 are preferably dimensioned to provide an overall lighted area for a given treatment area based on a range from the 5th percentile of corresponding female sizes to the 95th percentile of corresponding male sizes for that particular treatment area. The LED arrays 60 emit light at an appropriate wavelength according to the intended treatment or to activate the particular photoactivatable agent used in treatment or diagnosis. For example, when ALA is used as a precursor of a photoactivatable agent for the treatment of actinic keratosis, the LED arrays 60 preferably emit blue light having wavelengths at or above 400 nanometers (nm), for example, about 430 nm, about 420 nm or, for example, 417 nm. However, the LED arrays 60 may also emit visible light in other ranges of the spectrum, such as in the green and/or red ranges between 400 and 700 nm, for example, about 625 nm to 640 nm or, for example, 635 nm. For example, the LED arrays 60 may also emit light having wavelengths of 510 nm, 540 nm, 575 nm, 630 nm, or 635 nm. In addition, the LED arrays 60 may be configured to emit light continuously or the LED arrays 60 may be configured to flash the diodes on and off based on a predetermined interval. Furthermore, the LED arrays 60 may be configured such that only one wavelength of light (e.g., blue) is emitted. Alternatively, the LED arrays 60 may be configured such that two or more wavelengths of light are emitted from the arrays. For example, the LED arrays 60 may be configured to alternately emit blue light and red light for treatment purposes.

Figure 6:
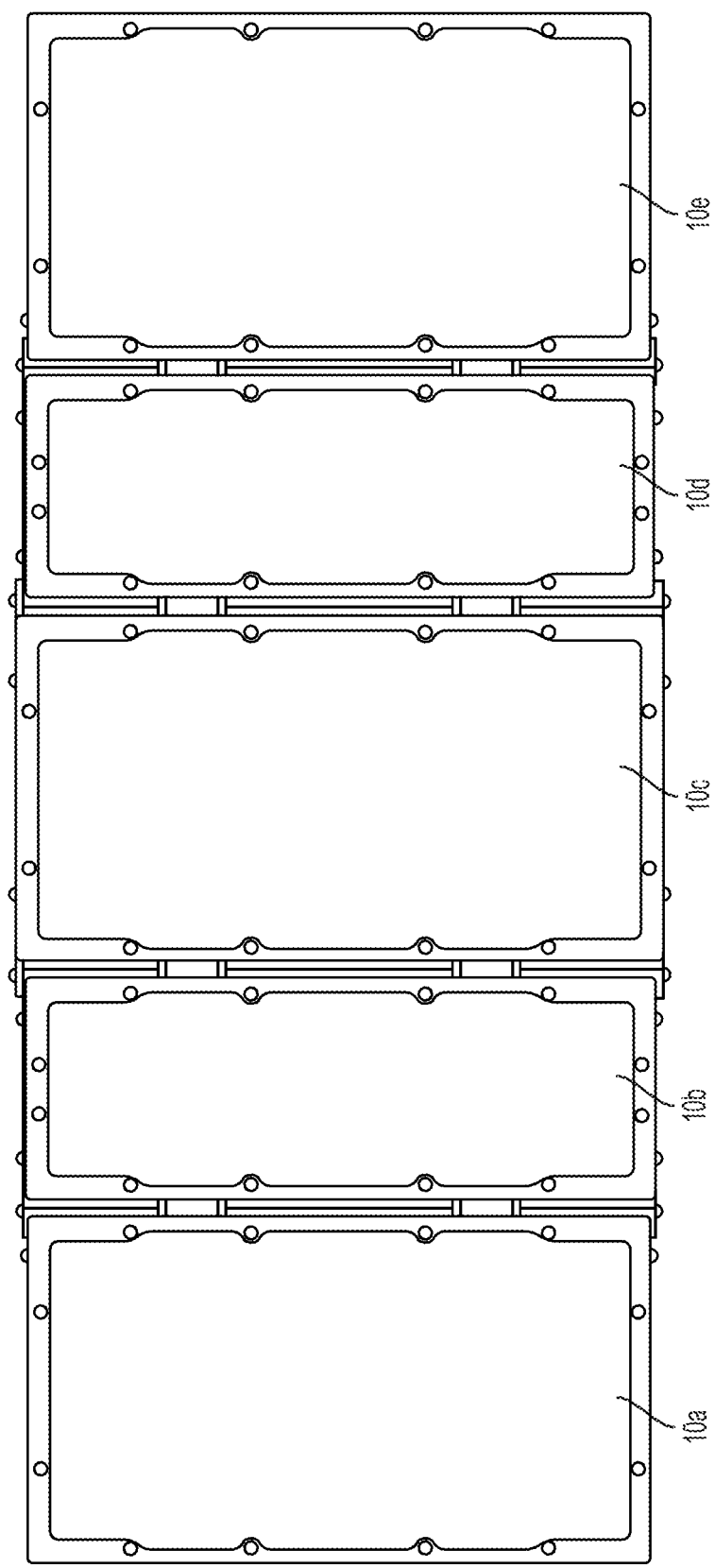
FIG. 6 shows a schematic view illustrating widths and lengths of individual panels of the main body of the illuminator of FIGS. 1A-1B.

As shown in FIGS. 1A-1B and 2A-2B, the five panels 10a-10e are of different widths relative to one another. In particular, in certain embodiments, three panels 10a, 10c, 10e are configured to have wider widths, while two panels 10b, 10d have smaller, narrower widths, each of the narrower widths of the two panels 10b, 10d being less than each of the wider widths of the three panels 10a, 10c, 10e. In some embodiments, the wider widths of the three larger panels 10a, 10c, 10e are approximately equal. In other embodiments, the wider widths of the three larger panels 10a, 10c, 10e are different relative to one another. In addition, the narrower widths of the two panels 10b, 10d may be approximately equal or may be different relative to one another. The panels are further arranged in an alternating configuration, with the narrower panels (e.g., 10b) positioned in between two wider panels (e.g., 10a, 10c). As shown in FIG. 6, in some embodiments, the narrower panels 10b, 10d are configured to have a width that is about 30% to 60% less than the width of the wider panels 10a, 10c, 10e. In other embodiments, the narrower panels 10b, 10d are configured to have a width that is about 30% to 50% less than the width of the wider panels 10a, 10c, 10e.

Figure 2A:
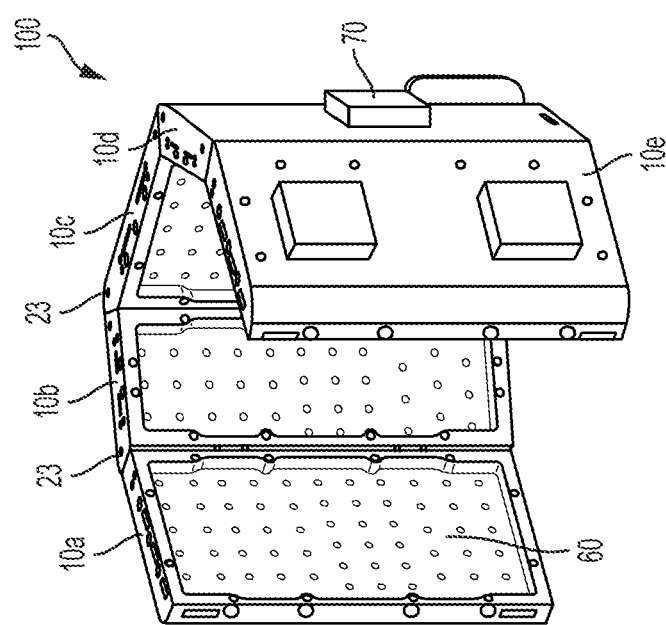

As shown in FIGS. 1A-1B and 2A-2B, the panels 10a-10e are rotatably connected by hinges 50. The hinges 50 may take the form of nested hinges, which may include hinges that substantially reduce or eliminate optical dead spaces. As shown in FIGS. 2A-2B, on at least one side of a panel, a tab 23 may extend out from both the top and bottom of the panel. The tabs 23 are configured such that a side of an adjacent panel may be received between the tabs 23, as shown in FIG. 2A. Thus, as best seen in FIGS. 2A-2B and 6, the height of the adjacent panel (e.g., panel 10a) is slightly smaller than the height of the tabbed panel (e.g., panel 10b) into which the adjacent panel is received. As shown in FIG. 6, the middle panel (i.e., panel 10c) is preferably configured as having the largest height, such that it is tabbed on both sides and may receive the sides of adjacent panels on each side. As seen in FIGS. 1A-1B, each of the tabs 23 further includes an opening to receive a bolt to connect adjacent panels together.

Figure 3A:
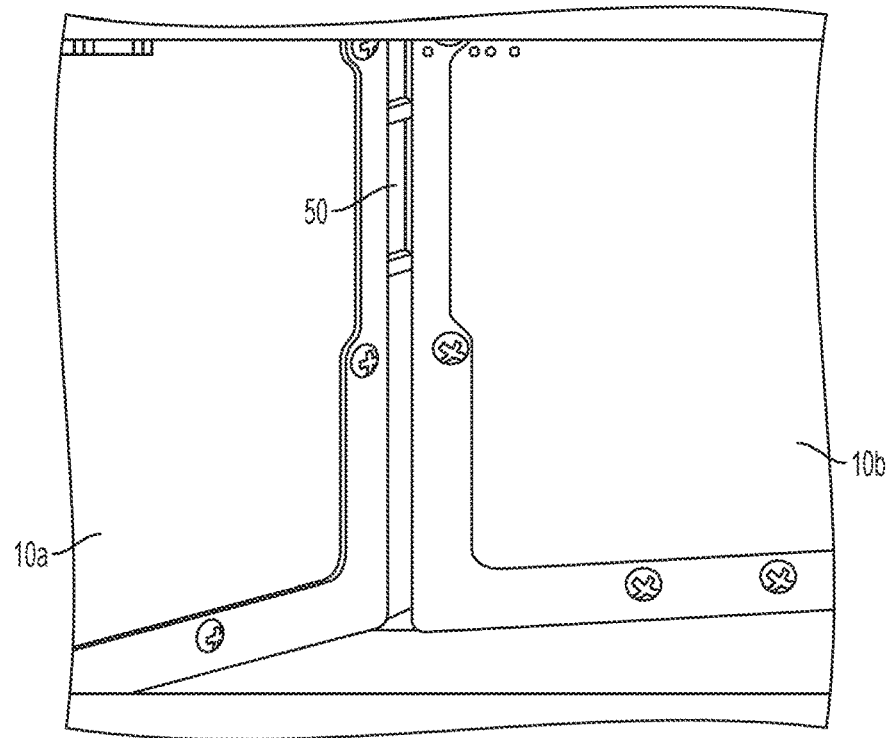
FIGS. 3A-3B show detailed views of the nested hinges of the main body of the illuminator of FIGS. 1A-1B.
Figure 3B:
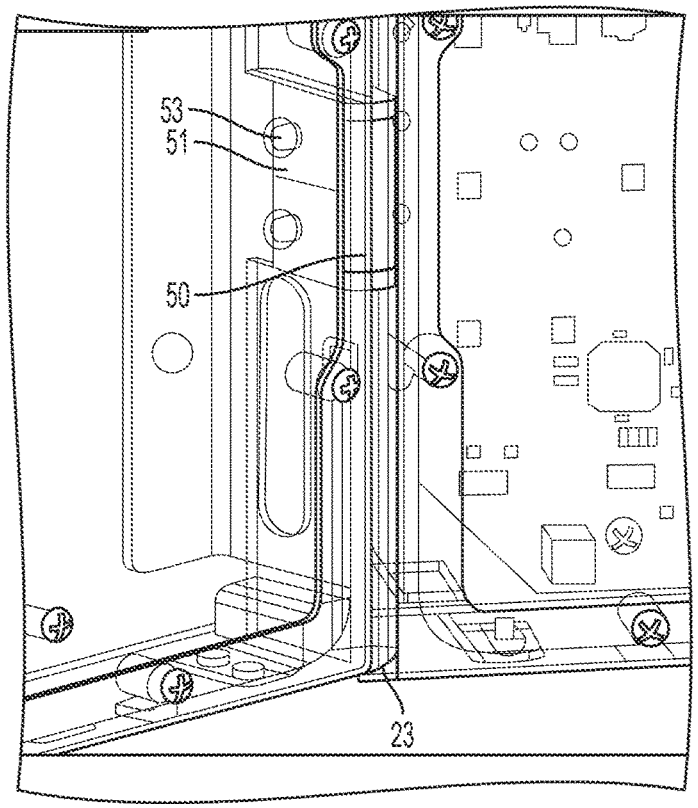

As shown in further detail in FIGS. 3A-3B, between the tabs 23 are the nested hinges 50, which are mounted to the inner side surfaces of adjacent panels (e.g., 10a, 10b) to allow for rotation of the panels. A flange 51 of the hinge 50 is mounted to the inner side surface of a panel via bolts 53.

The inner side surface of a panel may include a recess in which the flange 51 may be placed. The inner side surface of the panel may also include an additional recess to accommodate the joint of the hinge 50 such that the joint of the hinge 50 becomes substantially flush with an outer front surface of the panel. Such configurations may allow for the outside vertical edges of adjoining panels to be positioned closer to one another. By spacing the vertical edges of adjoining panels closer, optical dead spaces may be further reduced or eliminated. In addition, the hinges 50 together with the tabs 23 may reduce the number of pinch points present in the system.

Figure 4:
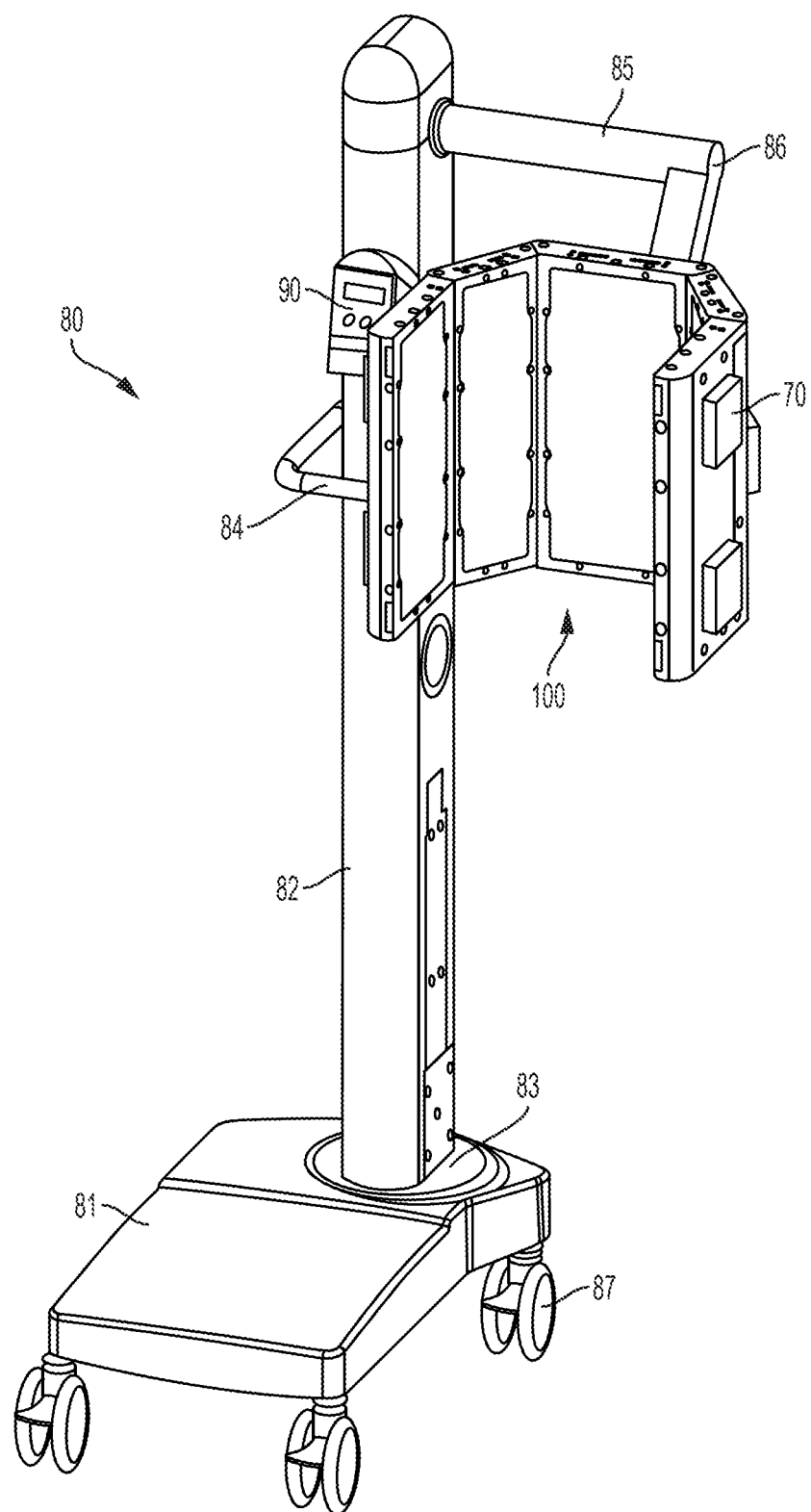
FIG. 4 shows a perspective view of the illuminator having the main body of FIGS. 1A-1B mounted to a stand.

As shown in FIGS. 1A-1B, the main body 100 of the illuminator may include a mounting head 40. The mounting head 40 may allow for the main body 100 to be mounted to a movable stand 80, which is shown in FIG. 4, to allow a user to easily move the main body 100 to the appropriate treatment position. The stand 80 includes a base 81 and a vertical pillar 82. The base 81 may further include wheels 87 at its bottom in order to allow the user to horizontally move the illuminator to an appropriate position. The wheels 87 may include locks, such that the stand 80 is prevented from further horizontal movement once positioned. In addition, the vertical pillar 82 may be attached to the base 81 at a pivot point 83. The pivot point 83 allows the vertical pillar 82 to be rotated to increase the range of positioning for the illuminator. At a top end, the vertical pillar 82 includes a connecting arm 85, which may serve as a mounting structure for the main body 100. The connecting arm 85 includes a hinge point 86 such that the main body 100 can be moved vertically relative to the stand 80. The vertical pillar 82 may also be configured as a telescopic structure, such that the user can change the height of the vertical pillar 82. This allows for an increased range of vertical movement for the main body 100, which can allow the user to position the main body 100 at lower portions of a treatment area, such as a patient's legs or feet. The stand 80 may also include a stabilization arm 84. Once the stand 80 and main body 100 is positioned, the stabilization arm 84 may be attached to the main body 100 to prevent unwanted movement of the main body 100 during treatment. As further shown in FIG. 4, a controller and power supply 90 is mounted to the stand 80 in order to supply electrical power to the main body 100 and allow the user to control the main body 100 for treatment purposes. Alternatively, the controller and power supply 90 may be directly mounted to the main body 100. In order to provide a cooling system for the LED arrays 60, one or more fans 70 may be mounted onto each of the panels, as shown in FIG. 4.

At least one control unit is also connected to the panels to regulate power to the lights to achieve the required uniformity and intensity for the target treatment. The control unit may be implemented as hardware, software, or a combination of both, such as a memory device storing a computer program and a processor to execute the program. Alternatively, each panel may have a dedicated control unit to regulate power to the individual LED array on a given panel to allow for more particular fine-tuning of the illuminator, which may further enhance uniformity and increase efficiency. For example, under Lambert's cosine law, light intensity at a given point on a "Lambertian" surface (such as skin) is directly proportional to the cosine of the angle between the incoming ray of light and the normal to the surface. Thus, a ray of light that is directed to the front of a curved surface (e.g., a head of a patient) will arrive in a substantially perpendicular manner to that area and will result in 100% absorbance. However, a ray of light that arrives at a side edge of the curved surface will arrive in a substantially parallel manner. According to Lambert's cosine law, the intensity, and thus absorption, of the light at the side edge will approach zero, making treatment at that area ineffective. Thus, a "fall off" of light exposure tends to occur at the edges of a curved surface. In addition, "fall off" increases as the distance between the light source and the point on the surface increases.

Configuring an illuminator to conform to the curved surface (e.g., a U-shaped configuration designed to "wrap around" the curvature of the surface) aids in reducing this effect and increases overall uniformity. However, to sufficiently increase uniformity, the light source should be larger relative to the target treatment area in order to fully encompass the body part to be treated and also provide light from all angles to any target point on the treatment area. In order to increase the uniformity of light exposure to the treatment area while maintaining a practical size of the illuminator, the LED arrays 60 may be individually configured to increase the intensity of light emitting from certain diodes to compensate for this fall-off effect.

Figure 5:
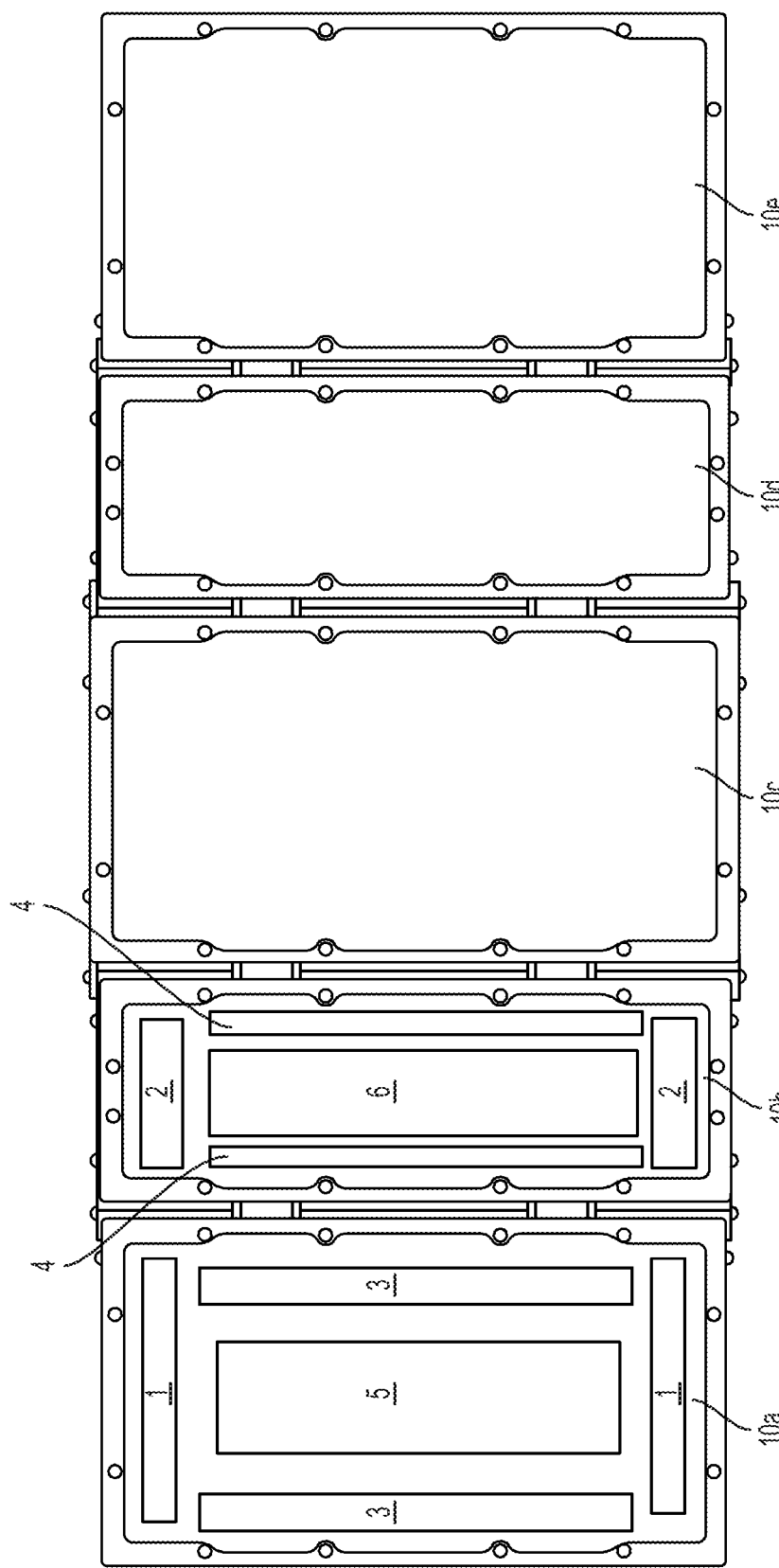
FIG. 5 shows a schematic view illustrating an addressable configuration of LEDs mounted on the main body of the illuminator of FIGS. 1A-1B.

An example in which the LED arrays 60 may be individually configured is shown in FIG. 5. Here, the LED arrays 60 are divided into three general areas, which may be described as "addressable strings." Areas 1, 3, and 5 correspond to an addressable string configuration that may be included in the wider panels 10*a*, 10*c*, and 10*e*, while areas 2, 4, and 6 correspond to an addressable string configuration that may be included in the narrower panels 10*b* and 10*d*. The current to each area is adjusted in order to adjust the intensity of light emitting from each of the areas. For example, a higher current may be supplied to areas 1 and 2 than the current supplied to areas 3 and 4 such that areas 1 and 2 emit a higher intensity of light than areas 3 and 4. Similarly, a higher current may be supplied to areas 3 and 4 than the current supplied to areas 5 and 6. Thus, a higher intensity of light is emitted overall from the edges, which may allow for a reduction in any fall-off effect. Alternatively, the illuminator may be configured to adjust each individual diode present in a given LED array 60, allowing for an even greater fine-tuning effect. Furthermore, by using either pre-programmed settings or sensors to detect the curvature of the surface to be treated, the LED arrays 60 can be individually configured to emit more intense light to only those areas that require it. This allows for an increase in uniformity of light exposure in an efficient manner as power output and/or light intensity is increased to only certain diodes, in accordance with need.

The addressable strings of the LED arrays 60 may also include varying amounts of individual diodes mounted within the particular area. For example, for the wider panels 10*a*, 10*c*, and 10*e*, 12 diodes may be mounted in each of areas 1, while 9 diodes may be mounted in each of areas 3 and 41 diodes may be mounted in area 5, resulting in a total of 83 individual diodes included within each of the wider panels 10*a*, 10*c*, and 10*e*. For the narrower panels 10*b* and 10*d*, 8 diodes may be mounted in each of areas 2, while 9 diodes may be mounted in each of areas 4, and 23 diodes may be mounted in area 6, resulting in a total of 57 individual diodes included within each of the narrower panels 10*b* and 10*d*. However, the number and arrangement of diodes included within each of the LED arrays 60 is not particularly limited. For example, the wider panels 10*a*, 10*c*, and 10*e* may each contain a total amount of diodes that ranges from about 80 diodes to about 350 diodes. Similarly, the narrower panels 10*b* and 10*d* may each contain a total amount of diodes that ranges from about 50 diodes to about 250 diodes. By varying the arrangement of the diodes within each of the addressable strings of the LED arrays 60, power output and/or the intensity of light emitted from a given array may be better controlled and fine-tuned.

In addition, individually regulating power to the LED arrays 60 can also contribute to the reduction or elimination of the optical dead spaces that may otherwise occur at the hinge points. Specifically, power output and/or the emitted light intensity may be increased close to the edges of the array that are closest to the nested hinges to compensate for the lack of light emitting from the meeting point of panels. The narrower panels 10b, 10d are also preferably operated at a higher power level and/or at a higher emitted light intensity compared to the wider panels 10a, 10c, 10e in order to provide additional fill-in light. Furthermore, individual power regulation may aid in compensating for manufacturing variance that can occur in individual diodes. Finally, by fine-tuning each array 60, the panels can be easily deployed for other applications as each array is specifically configurable to address the lighting needs of the specific application.

The illuminator may further include a timer, which can indicate to the user the appropriate length of exposure time for the particular treatment. The illuminator may also be programmed with pre-stored light dosing parameters to allow the user to select a desired treatment type. The pre-stored parameters may include, for example, pre-stored settings for exposure time, light intensity, and outputted wavelength. Based on the selected treatment, the illuminator is automatically configured to provide the correct lighting dosage by being supplied with the appropriate power output to achieve the required uniformity for the treatment. Alternatively, the illuminator can be provided with sensors that detect the size of the treatment area positioned in front of the illuminator. The sensors then determine the correct light dosing parameters based on the sensed treatment area. The illuminator may also further include actuators and may be programmed to be moved automatically depending on the selected treatment. Once a treatment is selected, the illuminator may be automatically positioned into the proper configuration by the actuators without requiring the user to move the system by hand. Alternatively, the sensors may detect the adjusted position of the illuminator manually set by the user. The detected position of the illuminator may then be used to indicate the intended treatment area. Correct light dosing parameters for the specific treatment area may then be provided based on the detected position set by the user.

The adjustable illuminator of the present invention allows for an infinite amount of configurations that can be adapted for the targeted treatment area. The configurations may range from a flat-plane emitter (as shown in FIGS. 1B and 2B) to a substantially U-shaped configuration (as shown in FIGS. 1A and 2A). The adjustable illuminator may also be configured such that the two end panels 10a, 10e can be pulled back relative to the three middle panels 10b, 10c, 10d, such that a smaller U-shaped configuration may be created by the middle panels. Thus, the adjustable illuminator allows for the treatment of additional areas of a patient's body. In other words, not only can the adjustable illuminator effectively deliver a uniform light intensity to traditional surfaces such as the face or scalp, but the adjustable illuminator can also provide a device that can easily be configured to treat other portions of a patient's body, in particular, those having smaller curved surfaces, such as the arms and legs. Moreover, the adjustable illuminator may also be easily positioned to deliver a uniform light intensity to larger treatment areas, such as the back or chest.

Figure 7:
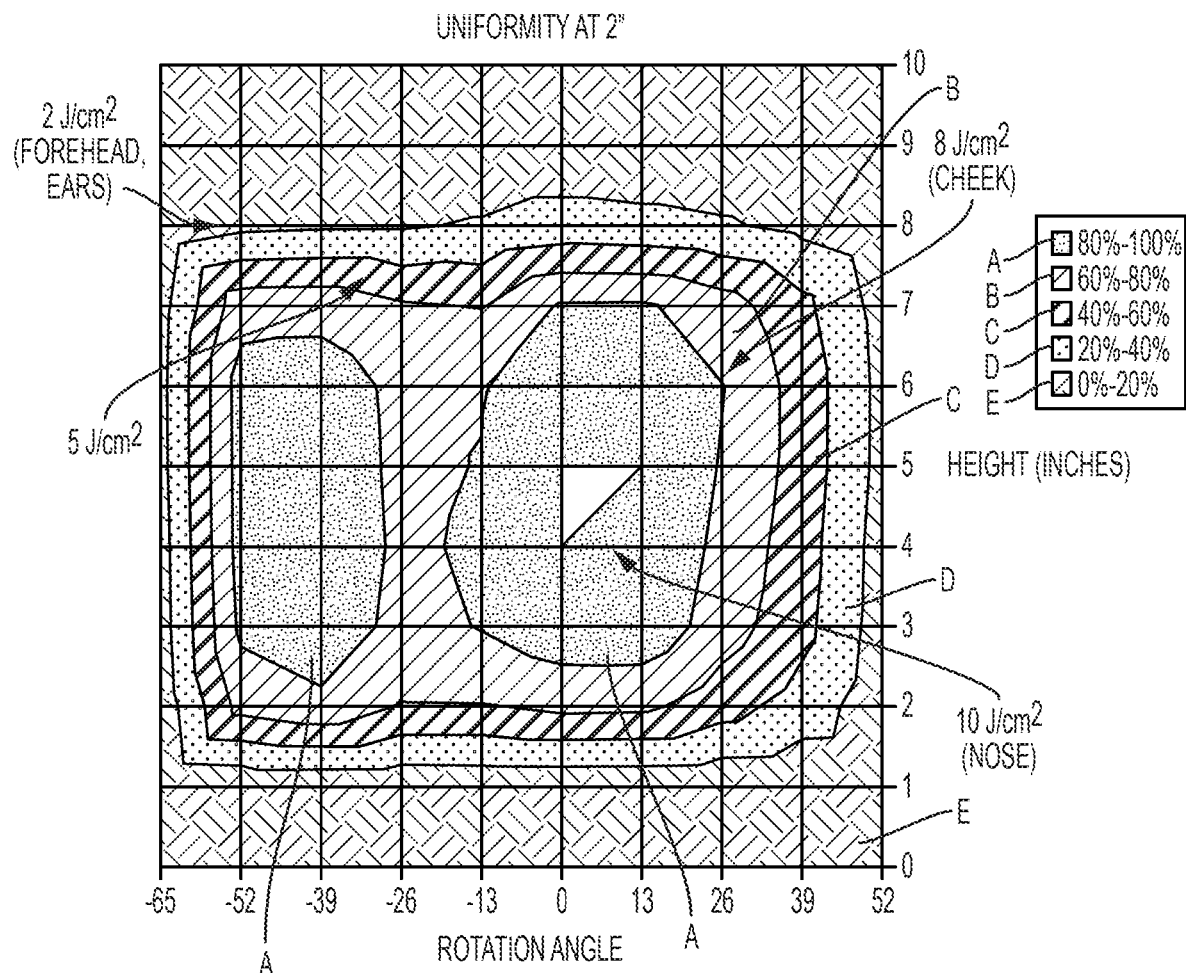
FIG. 7 shows a graph illustrating light dosage across a treatment area according to a conventional paneled illuminator.

As described above, the narrower panels 10b, 10d are dimensioned such that the panels act as "lighted hinges." Thus, when the wider panels 10a, 10c, 10e are adjusted into the desired form, the illuminator "bends" at the narrower panels 10b, 10d, where traditionally the "bend" would occur substantially at the hinge itself. Thus, instead of an unlighted "bent" portion as would occur in the conventional illuminator, the present illuminator provides a "bent" portion that is also configured to emit light, thereby helping to reduce optical dead space without requiring large amounts of power differentiation among the light sources of each panel to provide the required fill-in light. The effects of this configuration can be best seen in a comparison of FIGS. 7 and 8. FIG. 7 illustrates the light uniformity produced by a conventional illuminator, measured with a cosine response detector, which mimics the response of a patient's skin to the incident of light as described above, at a distance of two inches. Total light dose, in terms of $J/cm^2$, was measured based on emitted irradiance ($W/cm^2$) over time (in seconds). The targeted treatment area shown is a patient's head, where height is shown as the y-axis and rotation angle from the center of the emitting surface is shown as the x-axis. As can be seen in FIG. 7, higher light doses of about 10 $J/cm^2$ occur at the center of the face (for example, at region A), near the patient's nose, where the patient is facing closest to, and substantially perpendicular to, the middle-most panel. Total light dose then begins to drop as movement away from the center of the face occurs where the effects of cosine "fall-off" and optical dead spaces are more prevalent. For example, light dose is reduced by about 20% at the patient's cheek areas (for example, at region B), and by about 80% toward the outer boundaries of the patient's face (for example, at region E), such as the ears and forehead. Thus, as shown in FIG. 7, conventional adjustable illuminators utilizing equally-sized panels operating at the same power output level produce a varying field of light uniformity, making it undesirable and ineffective for those treatments requiring highly specific light uniformity.

Figure 8:
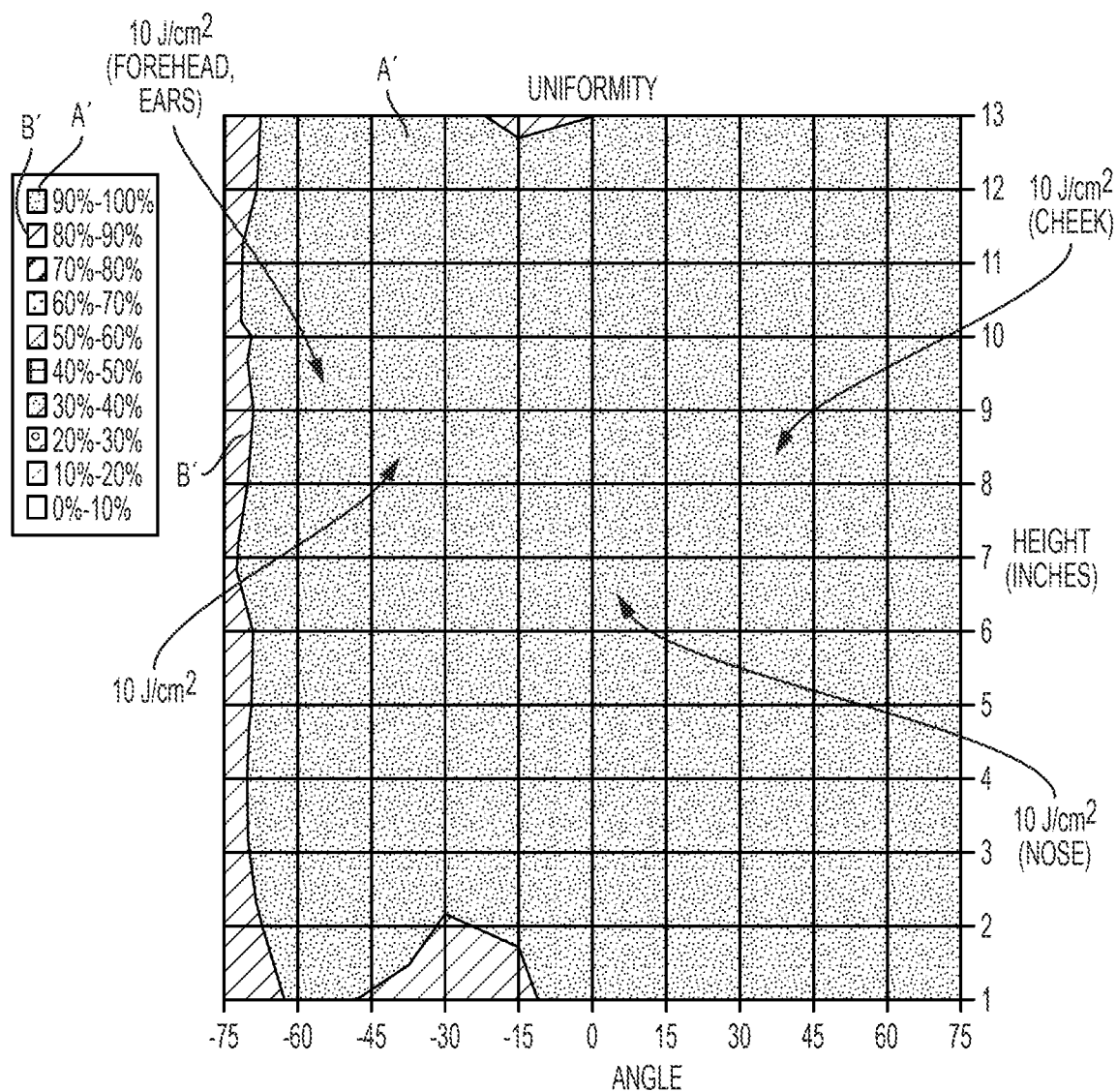
FIG. 8 shows a graph illustrating light dosage across the same treatment area as FIG. 7 using an illuminator according to one embodiment of the present invention.

FIG. 8, on the other hand, illustrates the light uniformity produced by an embodiment of the present invention. The targeted treatment area is the same as that measured in FIG. 7. However, compared to FIG. 7, the light output uniformity produced by the illuminator is greatly enhanced across the patient's face and exhibits little to no deviation from the light output measured in the center of the patient's face to the light output measured at the edges of the patient's face. For example, as shown in FIG. 8, total light doses of about 10 $J/cm^2$ (for example, at region A') occur across all regions of the face, including the center of the face (for example, the patient's nose), the patient's check areas, and the outer boundaries of the patient's cheek areas, such as the ears and forehead. Moreover, total light dose drops off minimally (for example, at region B') at the extreme outer boundaries of the patient's face. In one embodiment, the measured output over the active emitting area (over the entire active emitting area) is within 60% of the measured maximum (over the entire active emitting area) measured with a cosine response detector over all operation distances. More preferably, the measured output over the emitting area is within 70% of the measured maximum over a distance of two and four inches. Even more preferably, the measured output over the emitting area is within 80% of the measured maximum over a distance of two and four inches.

One example of a treatment method for precancerous lesions, such as actinic keratosis, by PDT utilizing an adjustable illuminator described above in conjunction with ALA will now be described.

Essentially anhydrous ALA is admixed with a liquid diluent just prior to its use. The ALA admixture is topically applied to the lesions using a point applicator to control dispersion of the ALA admixture. After the initial application of the ALA admixture has dried, one or more subsequent applications may be similarly applied. Approximately 2 mg/cm² of ALA is administered. Formation of photosensitive porphyrin and photosensitization of the treated lesions occurs over the next 14-18 hours, during which time exposure to direct sunlight or other bright light sources should be minimized. Between 14 and 18 hours after administration of the ALA, the lesions are irradiated by the adjustable illuminator according to the present invention. The illuminator irradiates the lesions with a uniform blue light for a prescribed period. According to a preferred treatment, the visible light has a nominal wavelength of 417 nm. The illuminator may irradiate the lesions with a uniform red light for a prescribed period. In certain embodiments, the illuminator irradiates the lesions with a uniform blue light for a first prescribed period and then irradiates the lesions with a uniform red light for a second prescribed period. For example, in some embodiments, the illuminator is configured to irradiate the lesions with a uniform blue light (e.g., 417 nm) at a low intensity (e.g., about 0.1 J/cm² to about 2 J/cm²) to photobleach, for example, protoporphyrin IX (PpIX) present at the surface of the patient's skin, and irradiate the lesions with a uniform red light (e.g., 635 nm) at a high intensity (e.g., about 30 J/cm² to about 150 J/cm²) to activate PpIX present at deeper layers of the patient's skin, thus avoiding potential damage to the upper layers of the patient's skin. The illuminator may be configured to simultaneously irradiate the patient's skin with the low intensity blue light and the high intensity red light or sequentially irradiate the patient's skin with the low intensity blue light and the high intensity red light. In certain embodiments, the illuminator is configured to irradiate the patient's skin with the low intensity blue light for about one hour to about three hours and irradiate the patient's skin with the high intensity red light for about 20 minutes to about 30 or 40 minutes, either at the same time the patient's skin is irradiated with the low intensity blue light or after the patient's skin has been irradiated with the low intensity blue light.

The invention thus provides a method for photodynamically diagnosing or treating a contoured surface of a patient, which includes providing the adjustable illuminator described above, placing the patient in the illuminator, and illuminating the patient to diagnose or treat the patient. The patient may be illuminated to treat actinic keratosis, acne, photo-damaged skin, cancer, warts, psoriasis, or other dermatological conditions. The method may also be used to remove hair and diagnose cancer.

Since the total light dose (J/cm²) is equal to irradiance (W/cm²) multiplied by time (sec), the only additional parameter that needs to be controlled for delivery of the correct treatment light dose is exposure time. This may be accomplished by the timer described above, which can control the electrical power supplied to the LED arrays 60 appropriately, and which can be set by the physician. Data has shown that 10 J/cm² delivered from a source with an irradiance density of 10 mW/cm², or an irradiance density of about 9.3 to about 10.7 mW/cm², produces clinically acceptable results for desired treatment areas (e.g., face, scalp, extremities). From the equation above, this light dose will require an exposure time of 1000 seconds (16 min. 40 sec). In addition, due to the addressable nature of the adjustable illuminator, the illuminator may be used to treat a patient at higher power such that less time is required for effective treatment. For example, the adjustable illuminator may deliver an irradiance density of 20 mW/cm² for an exposure time of 500 seconds (8 min. 20 sec) to deliver a clinically acceptable light dose of 10 J/cm². Alternatively, the adjustable illuminator may include higher power ranges, such as 30 mW/cm², over an exposure time resulting in a light dose of 10 J/cm². A selected light dose may also be administered by additionally or alternatively varying the irradiance density over treatment time.

Additional advantages and modifications will readily occur to those skilled in the art. Therefore, the invention in its broader aspects is not limited to the specific details and representative devices and methods, shown and described herein. Accordingly, various modifications may be made without departing from the spirit and scope of the general inventive concept as defined by the appended claims and their equivalents.

What is claimed is:

1. A system for photodynamically diagnosing or treating a patient, comprising:
    an illuminator comprising at least five panels connected by nested hinges on inner side surfaces of adjacent panels,
    light sources disposed on surfaces of the at least five panels, the illuminator being configured to uniformly illuminate a treatment surface of the patient via the light sources,
    one of the at least five panels positioned as a center panel configured to face the treatment surface, and two or more of the at least five panels being configured to be angled relative to the center panel,
    wherein each of the at least five panels has two first edges and two second edges shorter than the two first edges, and the light sources are arranged such that a higher intensity of light is emitted proximate the second edges compared to the intensity of light emitted not proximate the second edges.

2. The system of claim 1, wherein the illuminator is configured to uniformly illuminate the treatment surface when the treatment surface is at a distance of two to four inches from the illuminator.

3. The system of claim 1, wherein the illuminator is configured to output red light at a dose of about 30 J/cm² to about 150 J/cm².

4. The system of claim 1, wherein the illuminator is configured to output light at an irradiance density of 10 mW/cm² to 30 mW/cm².

5. The system of claim 1, wherein a plurality of the light sources are configured to emit light having a wavelength in a range of 400 nm to 700 nm.

6. The system of claim 1, further comprising a joint provided for one of the nested hinges, the joint positioned substantially flush with an outer front surface of one panel of the at least five panels.

7. The system of claim 1, further comprising a recess at an inner side surface of a panel configured to accommodate a hinge joint.

8. A method of photodynamically diagnosing or treating a patient, comprising:
    administering 5-aminolevulinic acid (ALA) to the patient;
    positioning an illuminator proximate to the patient, the illuminator comprising at least five panels connected by nested hinges on inner side surfaces of adjacent panels; and uniformly illuminating a treatment surface of the patient with light sources disposed on the at least five panels of the illuminator, wherein each of the at least five panels has two first edges and two second edges shorter than the two first edges, and the light sources are arranged such that a higher intensity of light is emitted proximate the second edges compared to the intensity of light emitted not proximate the second edges.

9. The method of claim 8, further comprising determining a size of the treatment surface of the patient using a sensor.

10. The method of claim 9, further comprising adjusting an overall light dose with a controller based on the determined size of the treatment surface.

11. The method of claim 9, further comprising adjusting positioning of panels with at least one actuator based on the determined size of the treatment surface.

12. The method of claim 8, further comprising determining a shape of the treatment surface of the patient using a sensor.

13. The method of claim 12, further comprising adjusting an overall light dose with a controller based on the determined shape of the treatment surface.

14. The method of claim 12, further comprising adjusting positioning of panels with at least one actuator based on the determined shape of the treatment surface.

15. The method of claim 8, wherein at least one panel includes tabs outwardly extending from a top side and a bottom side, the tabs being configured to receive an adjacent panel therein.

16. The method of claim 8, further comprising changing intensities of the light sources of the illuminator with a controller in accordance with information received from at least one sensor relating to a curvature of the treatment surface.

17. The method of claim 8, wherein at least one panel includes a recess configured to receive a flange of one of the nested hinges.

18. The method of claim 17, wherein the recess is positioned at an inner side surface of the at least one panel.

19. The method of claim 8, wherein the illuminator comprises at least three first panels having first widths, at least two second panels having second widths, wherein each of the second widths of the at least two second panels is narrower than each of the first widths of the at least three first panels; and wherein the at least three first panels and the at least two second panels are connected in an alternating manner such that each of the at least two second panels has a first lateral side connected to a respective one of the at least three first panels and a second lateral side connected to another respective one of the at least three first panels.

20. A system for photodynamically diagnosing or treating a patient, comprising:

an illuminator comprising at least five panels connected by nested hinges on inner side surfaces of adjacent panels, the nested hinges being configured so as to allow continuous illumination across the at least five panels, light sources disposed on surfaces of the at least five panels, the illuminator being configured to uniformly illuminate a treatment surface of the patient via the light sources, one of the at least five panels positioned as a center panel configured to face the treatment surface, and two or more of the at least five panels being configured to be angled relative to the center panel, wherein each of the at least five panels has two first edges and two second edges shorter than the two first edges, and the light sources are arranged such that a higher intensity of light is emitted proximate the second edges compared to the intensity of light emitted not proximate the second edges.

\* \* \* \* \*

UNITED STATES PATENT AND TRADEMARK OFFICE
CERTIFICATE OF CORRECTION

| | | |
|---|---|---|
| PATENT NO. | : 11,446,512 B2 | Page 1 of 1 |
| APPLICATION NO. | : 16/791004 | |
| DATED | : September 20, 2022 | |
| INVENTOR(S) | : Boyajian et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this
Eleventh Day of February, 2025

Coke Morgan Stewart
*Acting Director of the United States Patent and Trademark Office*